United States Patent [19]

Campbell

[11] 4,101,538

[45] Jul. 18, 1978

[54] NONAPEPTIDES AND METHODS FOR THEIR PRODUCTION

[75] Inventor: Alfred Campbell, Ann Arbor, Mich.

[73] Assignee: Warner-Lambert, Morris Plains, N.J.

[21] Appl. No.: 805,764

[22] Filed: Jun. 13, 1977

[51] Int. Cl.$^2$ .................... C07C 103/52; A61K 37/00
[52] U.S. Cl. .................. 260/112.5 LH; 260/112.5 R; 424/177
[58] Field of Search ............. 260/112.5 LH, 112.5 R; 424/177

[56] References Cited

U.S. PATENT DOCUMENTS 4,043,993  8/1977  Tinney et al. ............. 260/112.5 LH

*Primary Examiner*—Delbert R. Phillips
*Attorney, Agent, or Firm*—Stephen Raines; David B. Ehrlinger; Frank S. Chow

[57] ABSTRACT

New nonapeptides having the formula R-Gln-Trp-Ser-Tyr-Trp-Pro-Pro-Tyr(benzyl)-Ser(benzyl)-Y wherein R is a protective group and Y is amino, lower alkylamino or di(lower alkyl)amino.

2 Claims, No Drawings

NEW NONAPEPTIDES AND METHODS FOR THEIR PRODUCTION

SUMMARY AND DETAILED DESCRIPTION

The present invention relates to new peptide compounds that are useful as luteinizing hormone releasing factor antagonists and to methods for their production. More particularly, the invention relates to new nonapeptides that are represented by the formula

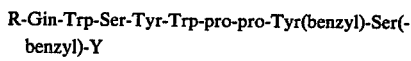  I wherein R is a protective group and Y is amino, lower alkylamino or di(lower alkyl)amino.

The preferred compounds of formula I are those wherein R is benzyloxycarbonyl, and Y is amino.

In formula I, the conventional symbols for amino acid residues of peptide compounds linked thereto are used and each is intended to have the following meaning: Pro, D-prolyl or L-prolyl; Trp, D-tryptophyl or L-tryptophyl; Ser; D-seryl or L-seryl; Tyr, D-tyrosyl or L-tyrosyl; Gln, D-glutaminyl or L-glutaminyl; Tyr(-benzyl), D-tyrosyl(benzyl) or L-tyrosyl(benzyl); and Ser(benzyl), D-seryl(benzyl) or L-seryl(benzyl). In addition, the term "lower alkyl" is intended to mean a straight, branched or cyclic hydrocarbon moiety of up to six carbon atoms, such as methyl, ethyl, isopropyl and cyclopropyl. A protective group is intended to mean a group usually employed in the area of peptides for protecting an amino function, such groups are disclosed in the following texts which are incorporated by reference: E. Schroder and K. Lubke, "The Peptides," Vol. I, Chapter 1., Academic Press, 1966 and J. Meienhofer in "Hormonal Proteins and Peptides", Vol. II, p. 227., Academic Press, 1973. These symbols and terms will also be used in the formulae that follow for other compounds and each such symbol or term should be understood to have the meaning given above.

In accordance with this invention, compounds of the formula I, wherein R and Y are as previously defined, are produced by reacting a compound of the formula R-Gln-Trp-Ser-Tyr-Trp-Pro-Pro-Tyr(benzyl)-Ser(-benzyl)-lower alkoxy    II wherein R is as previously defined and "lower alkoxy" is intended to mean an alkoxy group having a straight, branched or cyclic hydrocarbon moiety of up to 6 carbon atoms, such as methoxy, ethoxy and isopropoxy (preferably methoxy), with ammonia, lower alkylamine or di(lower alkyl)amine.

The reactions are conducted at temperatures of from about 5° to 100° C. for from three hours to four days, preferably about room temperature. Generally, a large excess of amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

The starting materials of formula II are produced by reacting an azide, represented by the formula

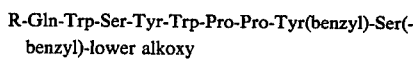  III with a compound of the formula

Trp-Pro-Pro-Tyr(benzyl)-Ser(benzyl)-lower alkoxy    IV in a non-reactive solvent medium, preferably dimethylformamide or a dimethylformamide-tetrahydrofuran mixture wherein R is as previously defined for formula I.

The azide of the formula III is prepared and used *in situ*.

The two components, III and IV, are generally reacted in approximately equimolar amounts at temperatures of from about −30° to about 30° C. for from 16 to 50 hours, although temperatures of from 30° to 50° C. may be used with a shortened reaction period.

The peptide azide compounds of the formula III that are used as a reactant in the foregoing process are normally prepared *in situ* by reacting a peptide hydrazide compound represented by the formula

  V wherein R is as previously described in formula I, with a lower alkyl nitrite, preferably isoamyl nitrite in the presence of an acid in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula V. The preparation of the azide is carried out at a temperature between −60° and 10° C. Following the *in situ* formation of the azide of formula III and prior to the further reaction of the peptide azide with the compound of formula IV to form the nonapeptide product I, a tertiary amine such as triethylamine is added to the reaction mixture to neutralize the acid used.

The peptide hydrazide compounds of formula V above are prepared by various methods. The hydrazide of the formula V, wherein R is as previously described in formula I, may be prepared by reacting an ester of the formula

  VI wherein R is as previously defined, with excess hydrazine (1:1.1 to 100) preferably in the form of its hydrate, in an organic solvent, such as dimethylformamide, methanol, ethanol, etc. The reaction is generally carried out at room temperature, although temperatures of from 5° to 100° C. may be employed for periods of from about 30 minutes to about 200 hours, preferably about 72 hours.

The esters of formula VI are prepared by reacting a compound of the formula

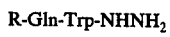  VII wherein R is as previously defined, with a compound having the formula

  VIII in the presence of a lower alkyl nitrite and an acid in the same manner that compounds of the formula II are prepared.

The compounds of the formula VIII is prepared by catalytically reducing the known compound of the formula

  IX using hydrogen and palladium-on-carbon in an inert solvent.

The hydrazides of the formula VII are prepared from esters of the formula

R-Gln-Trp-OCH₃     X wherein R is as previously defined according to the procedure for preparing the hydrazides of the formula V.

The compounds of the formula X are prepared by reacting protected glutamine with tryptophan methyl ester hydrochloride in the presence of diphenylphosphorazidate in a solvent, such as dimethylformamide at temperatures of from 5° C. to 25° C.

The esters of the formula IV are prepared by treating compounds of the formula t-butoxycarbonyl-Trp-Pro-Pro-Tyr(benzyl)-Ser(benzyl)-O-lower alkyl     XI with a large excess of trifluoroacetic acid in an inert solvent at about room temperature.

The compounds of the formula XI, are produced by removing a compound of the formula t-butoxycarbonyl-Trp-Pro-Pro-Tyr(benzyl)-Ser(benzyl)-resin     XII wherein said resin is a resin employed in solid phase peptide syntheses, such as those disclosed in a text by Stewart and Young, "Solid Phase Peptide Synthesis," W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the protected pentapeptide through a methyleneoxy bridge wherein the methylene group is attached to the polymeric portion of the resin and the oxygen atom is attached to the protected pentapeptide; by treating said resin of the formula XII with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

The complex resins of the formula XII are prepared by coupling a protected amino acid of the formula t-butoxycarbonyl-Trp-OH     XIII with complex resins of the formula Pro-Pro-Tyr(benzyl)-Ser(benzyl)-resin     XIV in an organic solvent, such as dichloromethane with the aid of dicyclohexylcarbodiimide. The three reactants may be used in about equimolar quantities, but excess amounts of the protected amino acid and dicyclohexylcarbodiimide are sometimes advantageous. The reaction is generally conducted at about room temperature for a period of from about fifteen minutes to about 20 hours.

The complex resins of the formula XIV are prepared by treating complex resins of the formula t-butoxycarbonyl-Pro-Pro-Tyr(benzyl)-Ser(benzyl)-resin     XV with a large excess of trifluoroacetic acid utilizing dichloromethane as the solvent at temperatures of from 20° to 30° C. for about 10 minutes followed by neutralization of the trifluoroacetic acid salt with a base such as triethylamine.

The complex resins of the formula XIV are prepared by coupling t-butoxycarbonyl-Pro-OH to complex resins of the formula Pro-Tyr(benzyl)-Ser(benzyl)-resin     XVI using the reaction procedure described for the preparation compounds of the formula XII.

The complex resins of the formula XVI are prepared by treating complex resins of the formula t-butoxycarbonyl-Pro-Tyr(benzyl)-Ser(benzyl)-resin     XVII with trifluoroacetic acid using the reaction procedure for the preparation of compounds of the formula XIV.

The complex resins of the formula XVII are prepared by coupling t-butoxycarbonyl-Pro-OH to comlex resins of the formula Tyr(benzyl)-Ser(benzyl)-resin     XVIII using the reaction procedure described for the preparation of compounds of the formula XII.

The complex resins of the formula XVIII are prepared by treating the complex resins of the formula t-butoxycarbonyl-Tyr(benzyl)-Ser(benzyl)-resin     XIX with trifluoroacetic acid using the reaction procedure for the preparation of compounds of the formula XIV.

The complex resins of the formula XIX are prepared by coupling t-butoxycarbonyl-Tyr(benzyl)-OH to complex resins of the formula Ser(benzyl)-resin     XX according to the procedure used for the preparation of compounds of formula XII.

The complex resins of the formula XX are prepared by treating the complex resins of the formula t-butoxycarbonyl-Ser(benzyl)-resin     XXI with trifluoroacetic acid using the reaction procedure for the preparation of compounds of the formula XIV.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Nonapeptides of this invention were screened for LRF antagonist activity in vitro using rat anterior pituitary cell cultures as described by Vale et. al. [Endocrinology, 91, 562 (1972)]. The inhibition of LRF (luteinizing hormone releasing factor) induced luteinizing hormone (LH) release into the culture medium is the endpoint in this *in vitro* bioassay.

| ACTIVITY TABLE FOR IN VITRO TEST IN RAT ANTERIOR PITUITARY CELL CULTURES | | | |
|---|---|---|---|
| Compound | Molar Conc. | LH Value ng./ml. | % LH Release Inhibition |
| $N^\alpha$-Benzyloxycarbonyl-L-glutaminyl-L-tryptophyl-L-seryl-L-tyrosyl-L-tryptophyl-L-prolyl-L-prolyl-O-benzyl-L-tyrosyl-O-benzyl-L-serinamide | $1 \times 10^{-7}$ $1 \times 10^{-8}$ | 52.33 47.20 | 29 37 |
| LRF Control | $5 \times 10^{-10}$ | 69.51 | |
| Saline Control | | 9.76 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, October 29, 1971, pages 511–512. Thus, the nonapeptides of this invention are useful in controlling ovulation and in restricting fertility.

The invention is illustrated by the following examples.

EXAMPLE 1

$N^\alpha$-Benzyloxycarbonyl-L-glutaminyl-L-tryptophyl-L-seryl-L-tyrosyl hydrazide, 0.6 g., is dissolved in 10 ml. of dimethylformamide containing 2 ml. of 2.5N hydrogen chloride in tetrahydrofuran. The solution is cooled to 0° C. and 0.1 g. of isopentylnitrite is added. The mixture is stirred at 0° C. for one hour and cooled to −60° C., triethylamine, 0.3 ml., is added followed by 0.6 g. of L-tryptophyl-L-prolyl-L-prolyl-O-benzyl-L-tyrosyl-O-benzyl-L-serinamide trifluoroacetate in 10 ml. of dimethylformamide. After three days at 0° C., the product $N^\alpha$-benzyloxycarbonyl-L-glutaminyl-L-tryptophyl-L-seryl-L-tyrosyl-L-tryptophyl-L-prolyl-L-prolyl-O-benzyl-L-tyrosyl-O-benzyl-L-serinamide is obtained after evaporation and chromatography on silica gel using methanol-acetonitrile (1:9); $[\alpha]_D^{23}$ −65.5° (c 1.02, methanol).

$N^\alpha$-Benzyloxycarbonyl-L-glutaminyl-L-tryptophyl-L-seryl-L-tyrosyl hydrazide is obtained from the corresponding methyl ester, 58.3 g., using 20 ml. of hydrazine hydrate with 500 ml. of dimethylformamide and allowing the solution to stand at 25° C. for four days. The product, 52.3 g., is isolated by filtration and washing with methanol; m.p. 251–253° C.

$N^\alpha$-Benzyloxycarbonyl-L-glutaminyl-L-tryptophyl-L-seryl-L-tyrosine methyl ester is prepared by deprotecting 62.7 g. of $N^\alpha$-benzyloxycarbonyl-L-seryl-L-tyrosine methyl ester [cf. Shioiri and Yamada, Chem. Pharm. Bull., 22, 859 (1974)] in a mixture of 550 ml. of methanol and 70 ml. of 2.35N hydrogen chloride in methanol in the presence of 3 g. of 5% palladium on carbon by stirring under an atmosphere of hydrogen for four hours. The catalyst is filtered and the mixture evaporated to yield 50.5 g. of L-seryl-L-tyrosine methyl ester hydrochloride which is suitable for use without further purification.

$N^\alpha$-Benzyloxycarbonyl-L-glutaminyl-L-tryptophyl hydrazide, 52.8 g., is dissolved in 800 ml. of dimethylformamide containing 150 ml. of 2.2N hydrogen chloride in tetrahydrofuran. The solution is cooled to −10° C. and 17 ml. of isopentylnitrite is added. The mixture is stirred at −15° ± 5° C. for one hour, cooled further to −30° and triethylamine 65 ml., is added followed by 38.5 g. of L-seryl-L-tyrosine methyl ester hydrochloride. After refrigeration overnight and evaporation, 58.7 g. of $N^\alpha$-benzyloxycarbonyl-L-glutaminyl-L-tryptophyl-L-seryl-L-tyrosine methyl ester is obtained after recrystallization from methanol; m.p. 238°–241° C.

$N^\alpha$-Benzyloxycarbonyl-L-glutaminyl-L-tryptophyl hydrazide is obtained from the corresponding methyl ester, 74.2 g., using 37.5 ml. of hydrazine hydrate with 150 ml. of dimethylformamide and 1.5 l. of methanol and allowing the solution to stand at 25° C. for 20 hours. The product, 66.6 g., is isolated by filtration and washing with methanol; m.p. 246°–248° C.

To a stirred mixture of $N^\alpha$-benzyloxycarbonyl-L-glutamine, 56 g., and L-tryptophan methyl ester hydrochloride, 56 g., in 300 ml. of dimethylformamide at 5° C. is added diphenylphosphorazidate, 47.5 ml., in 100 ml. of dimethylformamide dropwise over ten minutes followed by 61.6 ml. of triethylamine over one hour. The mixture is stirred in an ice bath for three hours and at room temperature for 18 hours. After evaporation the residue is dissolved in 1 l. of ethyl acetate and washed successively with 500 ml. of 1N hydrogen chloride solution, 500 ml. of a saturated solution of sodium bicarbonate and 500 ml. water. The ethyl acetate layer is separated, dried, evaporated and 74.2 g. of $N^\alpha$-benzyloxycarbonyl-L-glutaminyl-L-tryptophan methyl ester is obtained by recrystallization from methanol; m.p. 197°–198° C.

$N^\alpha$-t-Butoxycarbonyl-L-tryptophyl-L-prolyl-L-prolyl-O-benzyl-L-tyrosyl-O-benzyl-L-serinamide, 0.6 g., is treated with 10 ml. of trifluoroacetic acid. The solution is allowed to stand at room temperature for 30 minutes and then the excess trifluoroacetic acid is removed under reduced pressure. The residue is suspended in diethyl ether, filtered and washed with diethyl ether to yield 0.6 g. of L-tryptophyl-L-prolyl-L-prolyl-O-benzyl-L-tyrosyl-O-benzyl-L-serinamide trifluoroacetate. Finally the product is dried under reduced pressure at 50° C. and used without further treatment.

$N^\alpha$-t-Butoxycarbonyl-L-tryptophyl-L-prolyl-L-prolyl-O-benzyl-L-tyrosyl-O-benzyl-L-serine methyl ester, 0.5 g., is treated with 25 ml. of methanol saturated with ammonia for three days at room temperature. The product, $N^\alpha$-t-butoxycarbonyl-L-tryptophyl-L-prolyl-L-prolyl-O-benzyl-L-tyrosyl-O-benzyl-L-serinamide, 0.2 g., is obtained as a white glass after evaporation and chromatography on silica gel using methanol-ethyl acetate (1:4); $[\alpha]_D^{23}$ −69° (c 1.05, methanol).

$N^\alpha$-t-Butoxycarbonyl-L-tryptophyl-L-prolyl-L-prolyl-O-benzyl-L-tyrosyl-O-benzyl-L-serine resin, 20 g., is converted to the methyl ester yielding $N^\alpha$-t-butoxycarbonyl-L-tryptophyl-L-prolyl-L-prolyl-O-benzyl-L- tyrosyl-O-benzyl-L-serine methyl ester in the form of a glass; $[\alpha]_D^{23} -68°$ (c 1.05, methanol). The above resin is prepared according to the General Procedure given below using $N^{60}$-t-butoxycarbonyl-O-benzyl-L-serine resin which is successively reacted with 1) 8.9 g., 0.024 mol., of $N^\alpha$-t-butoxycarbonyl-O-benzyl-L-tyrosine and 5 g., 0.0242 mol., of dicyclohexylcarbodiimide, 2) 5 g., 0.0232 mol., of $N^\alpha$-t-butoxycarbonyl-L-proline and 5 g., 0.0242 mol., of dicyclohexylcarbodiimide, 3) 5 g., 0.0232 mol., of $N^\alpha$-t-butoxycarbonyl-L-proline and 5 g., 0.0242 mol., of dicyclohexylcarbodiimide, 4) 7.3 g., 0.024 mol., of $N^\alpha$-t-butoxycarbonyl-L-tryptophan and 5 g., 0.0232 mol., of dicyclohexylcarbodiimide.

$N^\alpha$-t-Butoxycarbonyl-O-benzyl-L-serine resin is obtained by refluxing 220 g., 0.352 mol., of 2% chloromethylated resin, 120 g., 0.41 mol., of $N^\alpha$-t-butoxycarbonyl-O-benzyl-L-serine and 35 g., 0.35 mol., of triethylamine in 2 l. of absolute ethanol for three days. Nitrogen analysis shows 0.00084 mol. per gram.

General Procedure for the Solid Phase Synthesis of Peptide Resins

The peptide resin is obtained by attaching an $\alpha$-amino-protected amino acid to a resin (usually a chloromethylated resin which is commercially available from Lab Systems, Inc., San Mateo, California). The peptide system is then constructed by de-protecting the $\alpha$-amino-protected amino acid resin and attaching an $\alpha$-amino-protected amino acid. Repetition of this process produces the peptide resin having the required number and sequence of the desired peptide. The terminal $\alpha$-amino protection is changed by de-protection and attaching the desired carboxylic terminal group. The solid phase synthesis procedure is described by J. M. Stewart, "Solid Phase Peptide Synthesis," W. H. Freeman and Co., 1969.

Each cycle of the procedure folows the scheme:
1. De-protection with excess 50% trifluoroacetic acid in dichloromethane.
2. Three washes with dichloromethane.
3. Neutralization of the trifluoroacetic acid salt with an excess of cold 10% triethylamine in dichloromethane.
4. Three washes with dichloromethane.
5. Fifteen to thirty minutes agitation with the $\alpha$-amino-protected amino acid which is present in up to a four-fold molar excess based on the resin nitrogen analysis. However, when a large excess of the $\alpha$-amino-protected amino acid is used it is agitated with the resin for 15 minutes and the excess recovered by draining the solution from the reactor.
6. Addition of dicyclohexylcarbodiimide at least equivalent to the $\alpha$-amino-protected amino acid in step 5 in dichloromethane followed by agitation for four to twenty hours. In the alternate method, a 3.3-fold excess of dicyclohexylcarbodiimide is used relative to the $\alpha$-amino-protected amino acid resin.
7. Three washes with dichloromethane.

I claim:
1. A nonapeptide of the formula

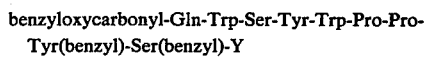

benzyloxycarbonyl-Gln-Trp-Ser-Tyr-Trp-Pro-Pro-Tyr(benzyl)-Ser(benzyl)-Y where Y is amino, lower alkylamino or di(lower alkyl)amino.

2. The nonapeptide of claim 1 having the name $N^\alpha$-benzyloxycarbonyl-L-glutaminyl-L-tryptophyl-L-seryl-L-tyrosyl-L-tryptophyl-L-prolyl-L-prolyl-O-benzyl-L-tyrosyl-O-benzyl-L-serinamide.

* * * * *